(12) United States Patent
Rezach et al.

(10) Patent No.: US 11,311,316 B2
(45) Date of Patent: Apr. 26, 2022

(54) SPINAL IMPLANT SYSTEM AND METHODS OF USE

(71) Applicant: Warsaw Orthopedic, Inc., Warsaw, IN (US)

(72) Inventors: William Alan Rezach, Covington, TN (US); Rodney Ray Ballard, Lakeland, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 17/012,404

(22) Filed: Sep. 4, 2020

(65) Prior Publication Data

US 2022/0071664 A1    Mar. 10, 2022

(51) Int. Cl.
*A61B 17/70* (2006.01)
*A61B 17/00* (2006.01)

(52) U.S. Cl.
CPC .. *A61B 17/7032* (2013.01); *A61B 2017/0088* (2013.01); *A61B 2017/00867* (2013.01); *A61B 2017/00933* (2013.01)

(58) Field of Classification Search
CPC ............ A61B 17/7032; A61B 17/7037; A61B 17/704; A61B 17/70–7052
See application file for complete search history.

(56) References Cited

U.S. PATENT DOCUMENTS

| | | | | |
|---|---|---|---|---|
| 5,190,543 A | * | 3/1993 | Schlapfer | A61B 17/7032 606/256 |
| 5,520,689 A | * | 5/1996 | Schlapfer | A61B 17/701 606/270 |
| 5,536,268 A | * | 7/1996 | Griss | A61B 17/7023 606/254 |
| 5,733,286 A | * | 3/1998 | Errico | A61B 17/7037 606/266 |
| 7,722,651 B2 | * | 5/2010 | Kwak | A61B 17/7037 606/265 |
| 7,749,258 B2 | * | 7/2010 | Biedermann | A61B 17/8605 606/308 |

(Continued)

FOREIGN PATENT DOCUMENTS

EP    2977017 A1    1/2016

OTHER PUBLICATIONS

European Patent Office, Notification of Transmittal of the International Search Report and the Written Opinion of the International Searching Authority, PCT/US2021/048621, dated Jan. 7, 2022.

*Primary Examiner* — Lynnsy M Summitt
(74) *Attorney, Agent, or Firm* — Sorell, Lenna & Schmidt, LLP

(57) ABSTRACT

A bone fastener comprises a first member comprising a first surface defining an implant cavity. The first member includes a first part being non-rotatable relative to the first surface and a second part including a second surface defining a portion of the implant cavity and a slot. A second member is configured to penetrate tissue and is connectable with the first member. The first member is rotatable relative to the second member in a first plane of a body and the second part is movable relative to the first part in a second plane of the body such that the first part is relatively translatable in the slot. Implants, systems, instruments and methods are disclosed.

18 Claims, 11 Drawing Sheets

(56) References Cited

U.S. PATENT DOCUMENTS

| | | | | |
|---|---|---|---|---|
| 7,766,944 | B2* | 8/2010 | Metz-Stavenhagen | A61B 17/7037 606/266 |
| 7,766,945 | B2* | 8/2010 | Nilsson | A61B 17/7037 606/266 |
| 7,951,172 | B2* | 5/2011 | Chao | A61B 17/7038 606/265 |
| 7,967,849 | B2* | 6/2011 | Carson | A61B 17/7038 606/267 |
| 7,967,850 | B2* | 6/2011 | Jackson | A61B 17/7032 606/301 |
| 8,012,183 | B2* | 9/2011 | Alain | A61B 17/7037 606/264 |
| 8,075,599 | B2* | 12/2011 | Johnson | A61B 17/7037 606/266 |
| 8,277,490 | B2* | 10/2012 | Freeman | A61B 17/7037 606/266 |
| 8,298,268 | B2* | 10/2012 | Marino | A61B 17/864 606/264 |
| 8,298,275 | B2* | 10/2012 | Rezach | A61B 17/7032 606/308 |
| 8,308,782 | B2* | 11/2012 | Jackson | A61B 17/7032 606/308 |
| 8,382,805 | B2* | 2/2013 | Wang | A61B 17/7037 606/267 |
| 8,430,917 | B2* | 4/2013 | Rezach | A61B 17/7037 606/306 |
| 8,470,009 | B1* | 6/2013 | Rezach | A61B 17/7038 606/300 |
| 8,556,938 | B2* | 10/2013 | Jackson | A61B 17/8685 606/269 |
| 8,632,571 | B2* | 1/2014 | Kraus | A61B 17/704 606/264 |
| 8,764,804 | B2* | 7/2014 | Rezach | A61B 17/7038 606/267 |
| 8,845,691 | B2* | 9/2014 | Renaud | A61B 17/7034 606/264 |
| 8,852,239 | B2* | 10/2014 | Jackson | A61B 17/7032 606/267 |
| 8,998,965 | B2* | 4/2015 | Biedermann | A61B 17/7032 606/305 |
| 9,044,272 | B2* | 6/2015 | Shaffrey | A61B 17/7002 606/266 |
| 9,326,795 | B2* | 5/2016 | Beaurain | A61B 17/701 |
| 9,968,378 | B1* | 5/2018 | Johnson | A61B 17/7037 |
| 9,974,569 | B2* | 5/2018 | Lehmann, Jr. | A61B 17/7032 |
| 10,130,395 | B2* | 11/2018 | Left | A61B 17/7037 |
| 10,555,760 | B2* | 2/2020 | Buttermann | A61B 17/7037 |
| 2004/0260284 | A1* | 12/2004 | Parker | A61B 17/7037 606/276 |
| 2006/0271193 | A1* | 11/2006 | Hartmann | A61B 17/7032 623/17.11 |
| 2007/0043358 | A1* | 2/2007 | Molz | A61B 17/7037 623/17.16 |
| 2007/0270831 | A1* | 11/2007 | Dewey | A61B 17/7037 606/86 A |
| 2009/0312804 | A1* | 12/2009 | Gamache | A61B 17/704 606/308 |
| 2011/0106173 | A1* | 5/2011 | Lindemann | A61B 17/7038 606/302 |
| 2011/0106180 | A1* | 5/2011 | Miller | A61B 17/7032 606/308 |
| 2011/0106193 | A1* | 5/2011 | Alferness | A61F 2/2481 607/5 |
| 2011/0257690 | A1* | 10/2011 | Rezach | A61B 17/7082 606/302 |
| 2015/0025579 | A1* | 1/2015 | Biedermann | A61B 17/7032 606/266 |
| 2016/0262801 | A1* | 9/2016 | Rezach | A61B 17/7038 |
| 2017/0042584 | A1 | 2/2017 | Lehmann, Jr. et al. | |
| 2019/0183535 | A1* | 6/2019 | May | A61B 17/702 |

* cited by examiner

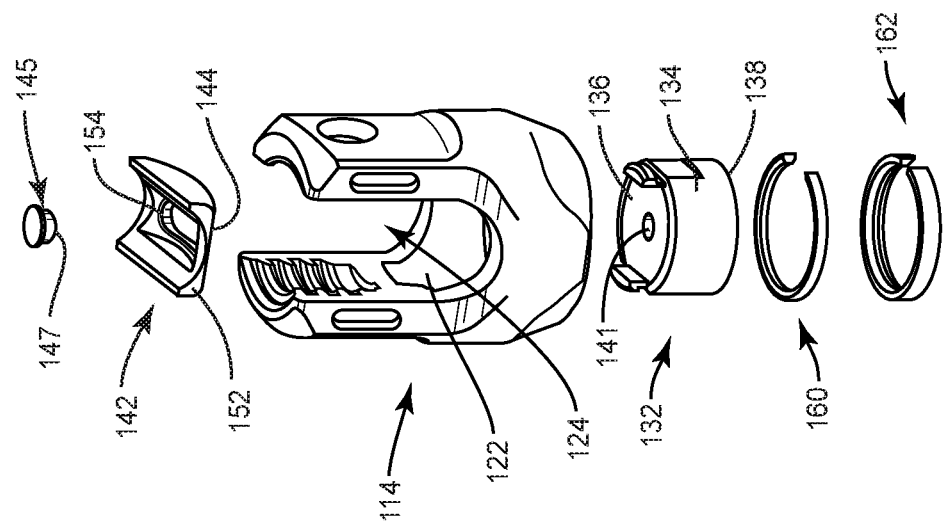
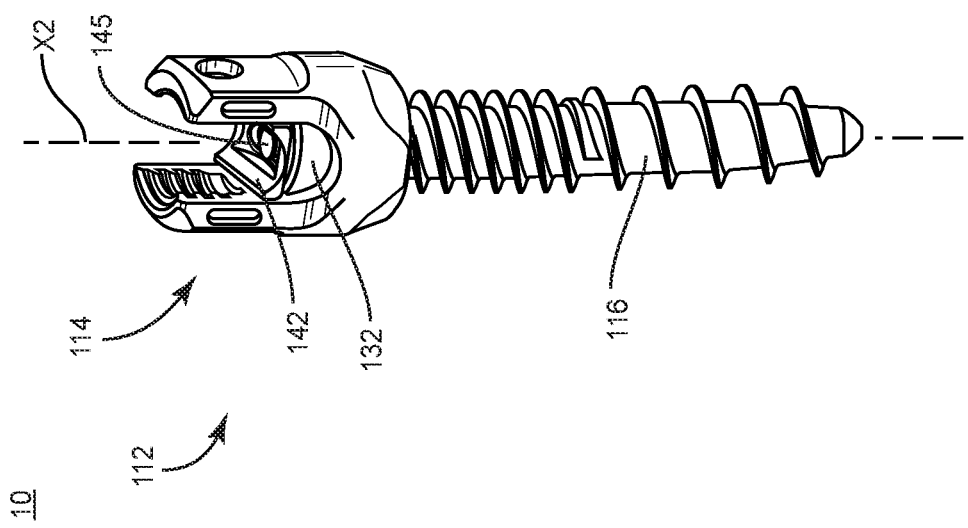

SPINAL IMPLANT SYSTEM AND METHODS OF USE

TECHNICAL FIELD

The present disclosure generally relates to medical devices for the treatment of spinal disorders, and more particularly to a spinal implant system including a bone fastener and a related method.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a bone fastener is provided. The bone fastener comprises a first member comprising a first surface defining an implant cavity. The first member includes a first part being non-rotatable relative to the first surface and a second part including a second surface defining a portion of the implant cavity and a slot. A second member is configured to penetrate tissue and is connectable with the first member. The first member is rotatable relative to the second member in a first plane of a body and the second part is movable relative to the first part in a second plane of the body such that the first part is relatively translatable in the slot. In some embodiments, implants, systems, instruments and methods are disclosed.

In one embodiment, the bone fastener comprises a receiver comprising an inner surface defining an implant cavity. The receiver includes a crown fixed in rotation with the inner surface and a saddle including a wall defining a portion of the implant cavity and a slot. A bone screw shaft includes a head having a mating element engageable with the crown. The receiver is rotatable relative to the shaft in a transverse plane of a body and the saddle is movable relative to the crown in a sagittal plane of the body such that the crown is translatable in the slot.

In one embodiment, a spinal implant system is provided. The spinal implant system comprises a plurality of alternate implant receivers including at least one implant receiver. The at least one implant receiver comprises an inner surface defining an implant cavity and includes a crown being non-rotatable relative to the inner surface. A saddle defines a portion of the implant cavity and a slot. A bone screw shaft includes a head engageable with an implant receiver such that the shaft is compatible with the plurality of implant receivers. The receiver is rotatable relative to the shaft in a transverse plane of a body and the saddle is movable relative to the crown in a sagittal plane of the body such that the crown is translatable in the slot.

BRIEF DESCRIPTION OF THE DRAWINGS

The present disclosure will become more readily apparent from the specific description accompanied by the following drawings, in which:

FIG. 12 is a perspective view of components of one embodiment of a spinal implant system in accordance with the principles of the present disclosure;

FIG. 13 is a perspective view of components of the system shown in FIG. 12 with parts separated;

DETAILED DESCRIPTION

Figure 1:
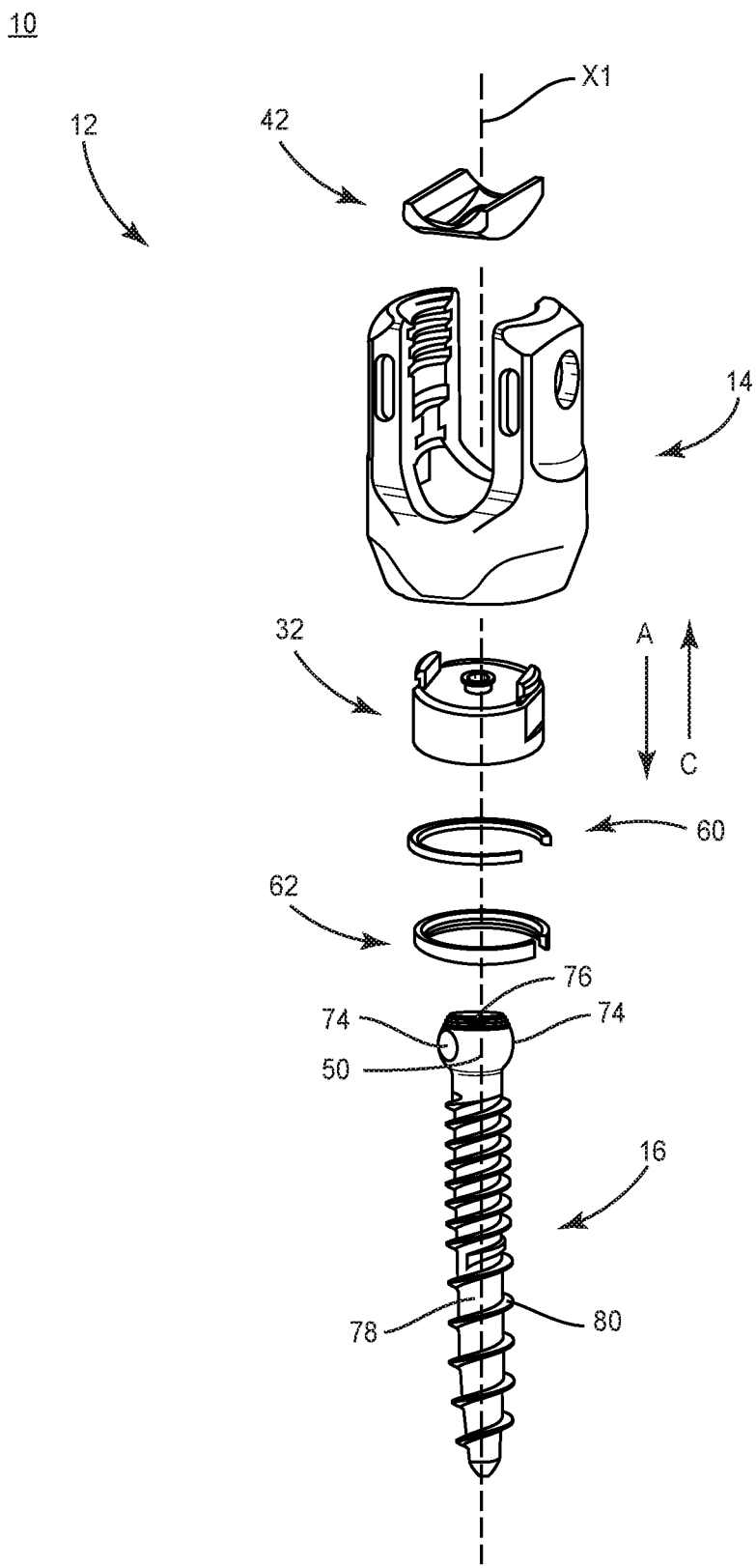
FIG. 1 is a perspective view of components of one embodiment of a spinal implant system in accordance with the principles of the present disclosure with parts separated.

The exemplary embodiments of a surgical system and related methods of use disclosed are discussed in terms of medical devices for the treatment of musculoskeletal disorders and more particularly, in terms of a spinal implant system including a bone fastener. In one embodiment, the present spinal implant system includes an implant comprising a bone fastener, for example, a bone screw. In some embodiments, the systems and methods of the present disclosure are employed with a spinal joint fusion or fixation procedure, for example, with a cervical, thoracic, lumbar and/or sacral region of a spine.

In some embodiments, the spinal implant system includes an implant, for example, a bone screw. In some embodiments, the bone screw includes a receiver, a crown, a saddle defining a slot and a bone screw shaft. In some embodiments, the bone screw shaft includes a head having a mating element engageable with the crown. In some embodiments, the receiver is rotatable relative to the shaft in a transverse plane of a body and the saddle is movable relative to the crown in a sagittal plane of the body such that the crown is translatable in the slot.

In some embodiments, the spinal implant system includes a pedicle screw comprising a selectively coupled transverse, sagittal adjusting receiver. In some embodiments, the spinal implant system includes a receiver that is configured to accommodate transverse and sagittal anatomical differences. In some embodiments, the spinal implant system comprises a modular system including an array of members, for example, receivers that are selectively coupled to members, for example, bone screw shafts. In some embodiments, the spinal implant system facilitates sagittal correction and/or manipulation when a spinal rod is disposed with a receiver.

In some embodiments, the spinal implant system includes a bone screw that includes a screw shaft including a head. In some embodiments, the head is configured in an array of configurations. In some embodiments, the array of head configurations allow surgeons flexibility and alternatives in the operating room such that an array of receivers can be connected with the head. In some embodiments, the array of head configurations reduces the amount of inventory transported into the operating room for a procedure.

In some embodiments, the spinal implant system includes an implant, for example, a transverse uni-axial, sagittal adjusting screw. In some embodiments, the screw includes a saddle. In some embodiments, the saddle is configured for sagittal adjustment and/or movement forgiveness of a spinal implant, for example, a spinal rod. In some embodiments, the screw includes a head attachment. In some embodiments, the head attachment is a universal head attachment. In some embodiments, transverse adjustment and/or movement forgiveness is achieved via the universal head attachment. In some embodiments, the universal head attachment is configured in a transverse plane to facilitate active correction, for example, through manipulation of the sagittal plane to adjust the head into a desired correction.

In some embodiments, the spinal implant system includes a bone screw that includes a screw shaft including a head. In some embodiments, the head includes a mating element that includes flats that are engageable with a crown. In some embodiments, the flats and the crown interface in a keyed connection such that the shaft pivots through only the transverse plane relative to a receiver.

In some embodiments, the spinal implant system includes a crown and a saddle. In some embodiments, the crown and the saddle are configured for engagement. In some embodiments, the crown and the saddle are configured for an interference fit, for example, a snap fit engagement. In some embodiments, during manufacturing, the saddle is positioned with the crown via a manufacturing press. In some embodiments, the crown is configured to provide an increase in axial grip on a spinal rod and an increase in flexion and/or extension strength.

In some embodiments, the spinal implant system comprises a crown, a saddle and a retention member and/or projection. In some embodiments, the retention member and/or projection includes, for example, a welded element.

In some embodiments, the retention member and/or projection is configured to retain the saddle with the crown and to limit angular rotation of the saddle when disposed in the receiver. In some embodiments, the retention member and/or projection is welded to the crown. In some embodiments, the retention member and/or projection includes a press fit or a threaded connection with the crown and/or the saddle.

In some embodiments, the spinal implant system comprises a modular system that includes a bone fastener including an array of members, for example, bone screw shafts that can be selectively coupled to members, for example, receivers. In some embodiments, the spinal implant system comprises a selectively coupled bone fastener that can be assembled on a surgical table or in-situ. In some embodiments, the bone fastener is selectively coupled with a non-instrumented and/or manual assembly. In some embodiments, the non-instrumented assembly comprises manually engaging a screw shaft with a head/receiver of the bone fastener. In some embodiments, the non-instrumented assembly comprises manually engaging the screw shaft in a pop-on engagement with the head/receiver of the bone fastener. In some embodiments, a force required to manually engage a screw shaft with a head/receiver of the bone fastener in a non-instrumented assembly is in a range of 2 to 50 N. In some embodiments, a force required to manually engage a screw shaft with a head/receiver of the bone fastener in a non-instrumented assembly is in a range of 5 to 10 N. In some embodiments, this configuration provides manually engageable components of a bone fastener that are assembled without instrumentation, and subsequent to assembly, the assembled components have a selected pull-out strength and/or can be pulled apart, removed and/or separated with a minimum required force.

In some embodiments, the head assembly includes a ring disposed with an implant receiver connected with a screw shaft assembly. In some embodiments, the ring is configured to snap onto the screw shaft assembly. In some embodiments, the force required to snap the ring onto the screw shaft assembly is in a range of 2 to 50 N. In some embodiments, the force required to snap the ring onto the screw shaft assembly is in a range of 5 to 10 N.

In some embodiments, the present disclosure may be employed to treat spinal disorders, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a bone fastener, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-17, there are illustrated components of a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Figure 17:
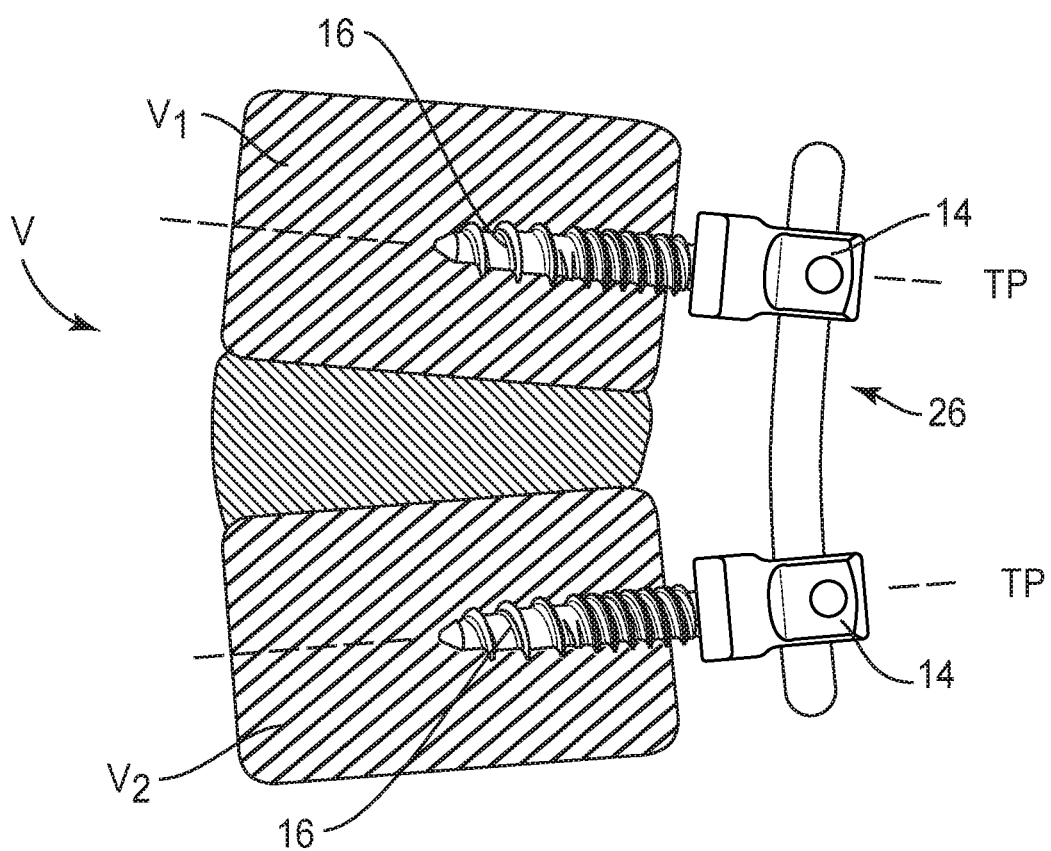
FIG. 17 is a side view of components of one embodiment of a spinal implant system in accordance with the principles of the present disclosure disposed with vertebrae shown in cross section.

Spinal implant system 10 includes a spinal implant, for example, a bone fastener 12. Bone fastener 12 includes a proximal member, for example, a receiver 14 that is connectable with a distal member, for example, a bone screw shaft 16 that is configured to penetrate vertebral tissue, as shown in FIG. 1. Receiver 14 is rotatable relative to shaft 16 in a plane, for example, a transverse plane TP of a body, as shown in FIG. 17. In some embodiments, receiver 14 is manually engageable with shaft 16 to connect receiver 14 with shaft 16. In some embodiments, receiver 14 is engageable with shaft 16 via an instrument. In some embodiments, receiver 14 is engageable with shaft 16 without an instrument and/or in a non-instrumented assembly.

Figure 2:
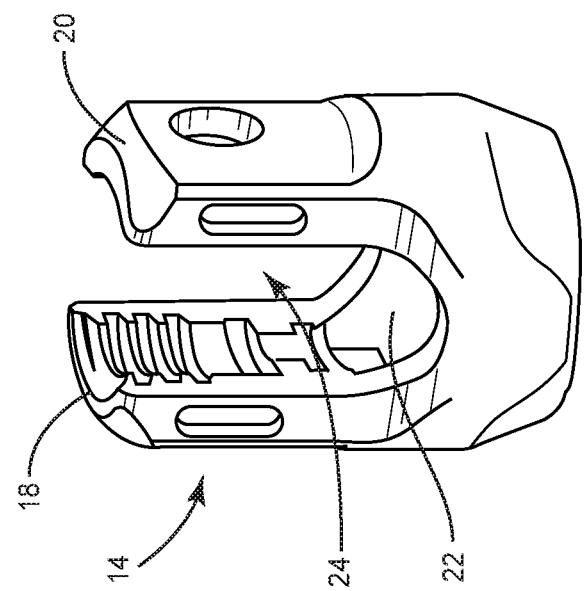
FIG. 2 is a perspective view of components of the system shown in FIG. 1.
Figure 7:
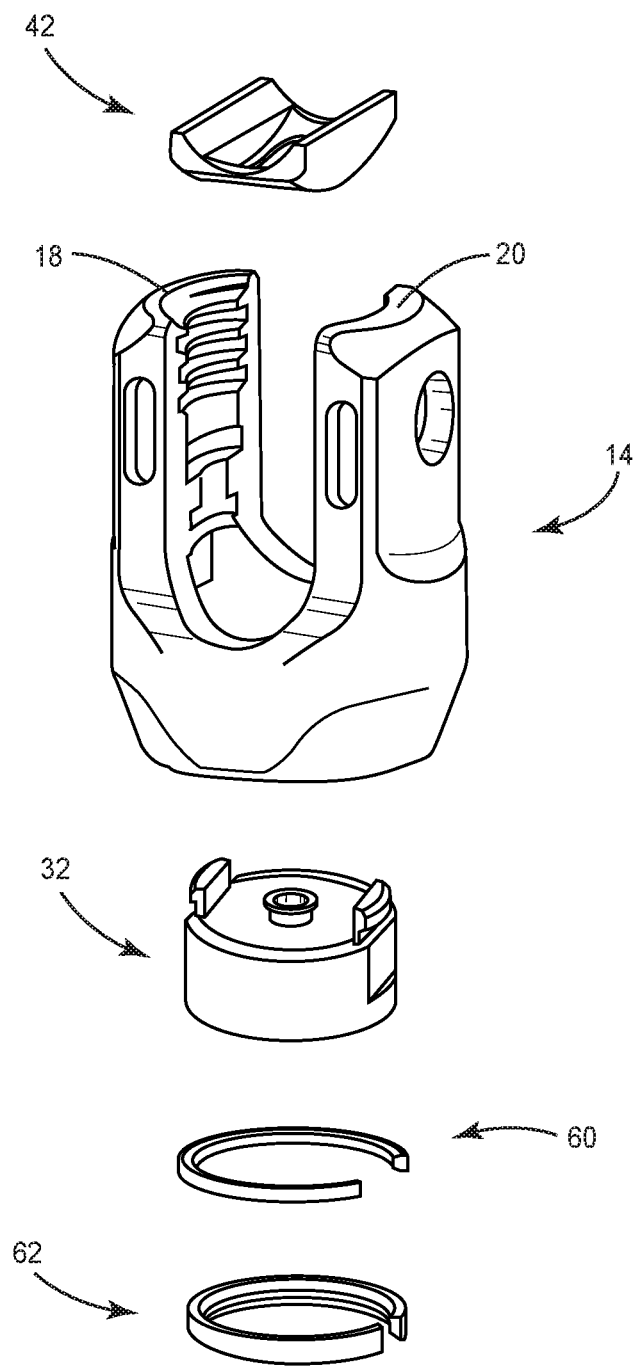
FIG. 7 is a perspective view of components of one embodiment of a spinal implant system in accordance with the principles of the present disclosure with parts separated.

Receiver 14 extends along and defines an axis X1, as shown in FIG. 1. Receiver 14 includes a pair of spaced apart arms 18, 20 that include an inner surface 22 that defines an implant cavity 24, as shown in FIG. 2. Cavity 24 is configured for disposal of a component of a spinal construct, for example, a spinal rod 26, as shown in FIGS. 14-17.

Arms 18, 20 each extend parallel to axis X1. In some embodiments, arm 18 and/or arm 20 may be disposed at alternate orientations, relative to axis X1, for example, transverse, perpendicular and/or other angular orientations such as acute or obtuse, coaxial and/or may be offset or staggered. Arms 18, 20 each include an arcuate outer surface extending between a pair of side surfaces. At least one of the outer surfaces and the side surfaces of arms 18, 20 have at least one recess or cavity therein configured to receive an insertion tool, compression instrument and/or instruments for inserting and tensioning bone fastener 12. In some embodiments, arms 18, 20 are connected at proximal and distal ends thereof such that receiver 14 defines a closed spinal rod 26 slot. In some embodiments, spinal rod 26 may be monolithically formed with receiver 14 or pre-assembled with receiver 14. In some embodiments, inner surface 22 and/or at least one of the inner surfaces of arms 18, 20 have at least one recess or cavity configured to receive an insertion tool, compression instrument and/or instruments for inserting and tensioning bone fastener 12.

Figure 10:
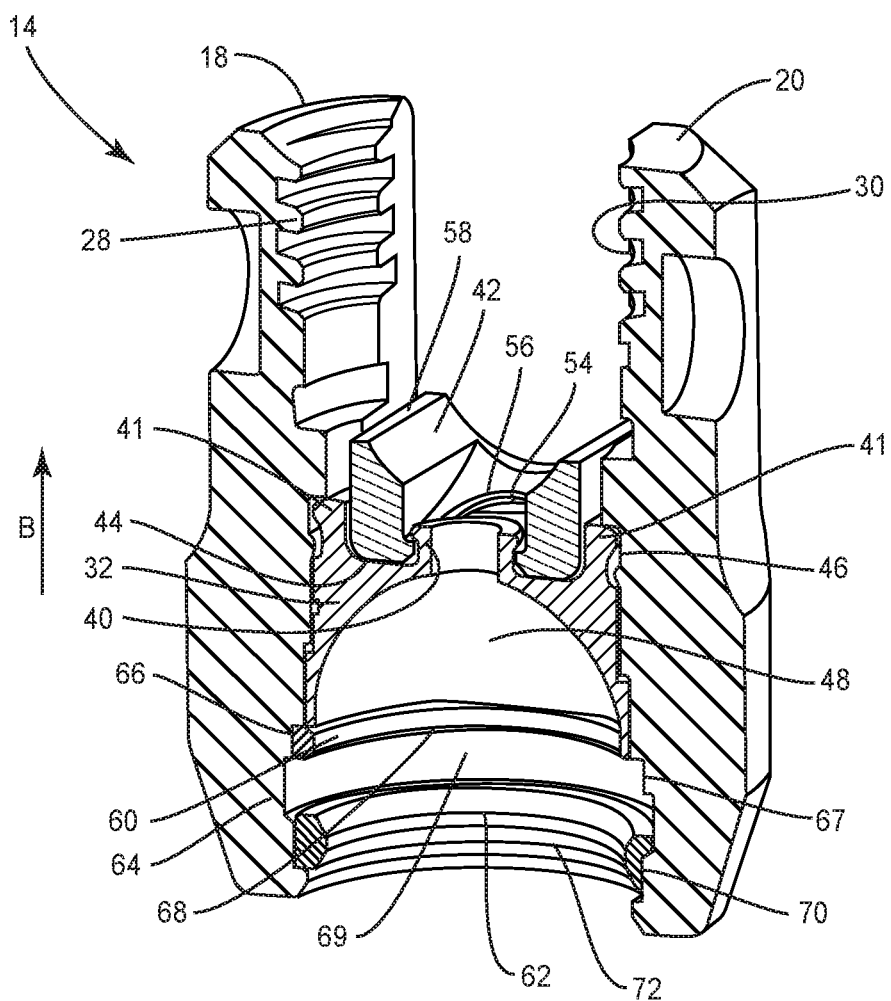
FIG. 10 is a cross section view of components of one embodiment of a spinal implant system in accordance with the principles of the present disclosure.

Cavity 24 is substantially U-shaped. In some embodiments, all or only a portion of cavity 24 may have alternate cross section configurations, for example, closed, V-shaped, W-shaped, oval, oblong, triangular, square, polygonal, irregular, uniform, non-uniform, offset, staggered, and/or tapered. A portion of surface 22 includes a thread form 28 located adjacent arm 18 and a thread form 30 located adjacent arm 20, as shown in FIG. 10. Thread forms 28, 30 are each configured for engagement with a coupling member, for example, a setscrew (not shown), to retain spinal rod 26 within cavity 24. In some embodiments, surface 22 may be disposed with the coupling member in alternate fixation configurations, for example, friction fit, pressure fit, locking protrusion/recess, locking keyway and/or adhesive. In some embodiments, all or only a portion of surface 22 may have alternate surface configurations to enhance engagement with spinal rod 26 and/or the setscrew, for example, rough, arcuate, undulating, mesh, porous, semi-porous, dimpled and/or textured. In some embodiments, receiver 14 may include alternate configurations, for example, closed, open and/or side access.

Figure 4:
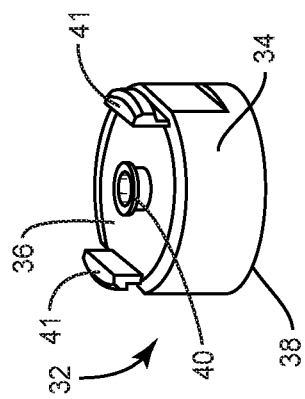
FIG. 4 is a perspective view of components of the system shown in FIG. 1.

Receiver 14 includes a part, for example, a crown 32 configured for disposal within cavity 24, as shown in FIGS. 4 and 10. Crown 32 is non-rotatable or fixed in rotation relative to surface 22. Crown 32 includes a circumferential wall 34 having an end surface 36 and an end surface 38, as shown in FIG. 4. In some embodiments, all or only a portion of surfaces 36, 38 may have alternate cross section configurations, for example, oval, oblong, triangular, square, polygonal, irregular, uniform, non-uniform, offset, staggered, and/or tapered.

Figure 3:
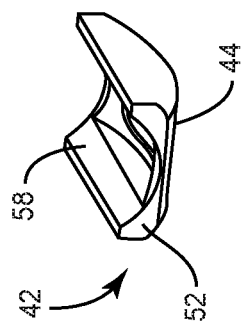
FIG. 3 is a perspective view of components of the system shown in FIG. 1.

Surface 36 defines a projection, for example, a circumferential flange 40, as shown in FIGS. 4 and 10. Flange 40 is configured for engagement with a surface 44 of a saddle 42, as shown in FIGS. 3 and 10 and described herein. In some embodiments, all or only a portion of flange 40 may have alternate cross section configurations, for example, oval, oblong, triangular, square, polygonal, irregular, uniform, non-uniform, offset, staggered, and/or tapered.

Surface 36 defines projections 41, as shown in FIGS. 4 and 10. Receiver 14 includes an undercut surface that defines a groove 46, as shown in FIG. 10. Projections 41 are configured for disposal with groove 46. Engagement of projections 41 with the undercut surface that defines groove 46 retains crown 32 with receiver 14. In some embodiments, all or only a portion of projections 41 may have alternate surface configurations, for example, rough, arcuate, undulating, mesh, porous, semi-porous, dimpled and/or textured. In some embodiments, surface 36 includes one or more projections 41.

Figure 11:
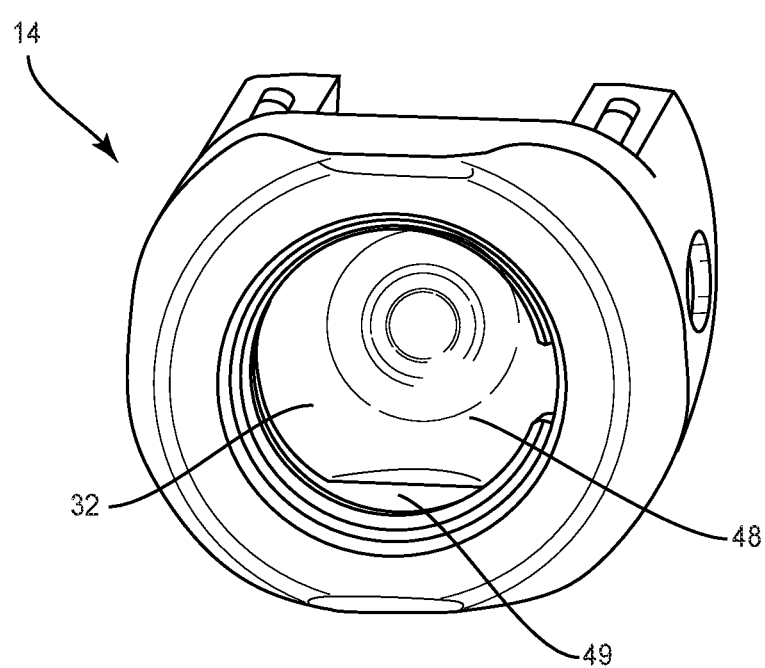
FIG. 11 is a perspective view of components of the system shown in FIG. 10.

Surface 38 defines a recess 48 including a mating element, for example, flats 49 configured for engagement with a mating element, for example, flats 74 of a head 50 of shaft 16, as shown in FIGS. 1, 10 and 11 and described herein. Flats 49 are configured to interface with flats 74 to resist and/or prevent rotation of receiver 14 about axis X1 in a perpendicular plane of motion. In this configuration, shaft 16 is free to rotate along a single axis and/or within a single plane relative to receiver 14. Head 50 is engageable with surface 38 and movable relative thereto such that shaft 16 is rotatable within a single plane, for example, a transverse plane TP of a body and/or vertebrae relative to receiver 14, as shown in FIG. 17. In some embodiments, all or only a portion of recess 48 may have alternate surface configurations, for example, rough, arcuate, undulating, mesh, porous, semi-porous, dimpled and/or textured.

In some embodiments, crown 32 includes an opening that is configured for disposal of a guidewire when receiver 14 is used in conjunction with a guidewire and is translated over the guidewire when implemented with a cannulated screw. In some embodiments, the opening is centrally located through crown 32.

Figure 9:
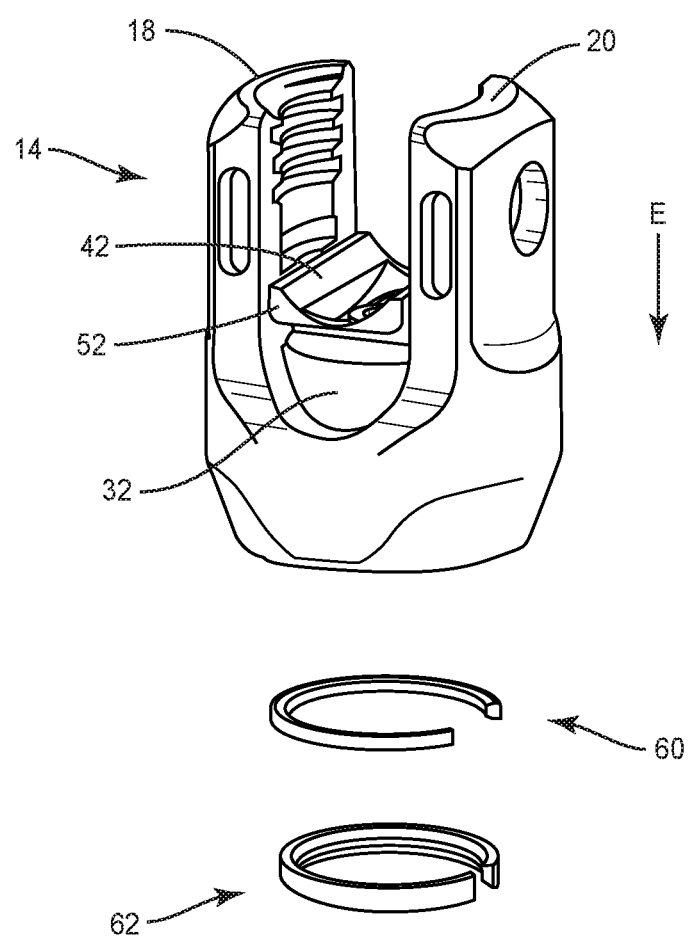
FIG. 9 is a perspective view of components of one embodiment of a spinal implant system in accordance with the principles of the present disclosure with parts separated.
Figure 14:
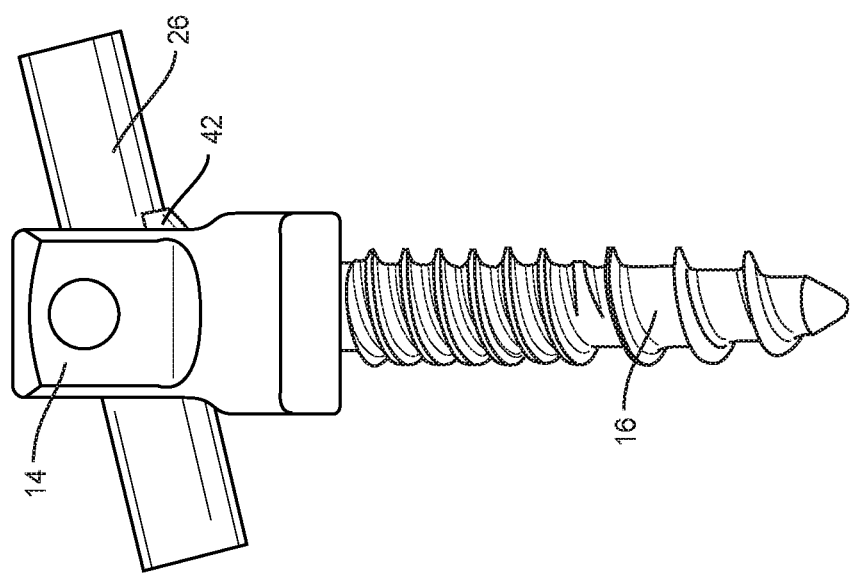
FIG. 14 is a side view of components of one embodiment of a spinal implant system in accordance with the principles of the present disclosure.
Figure 16:
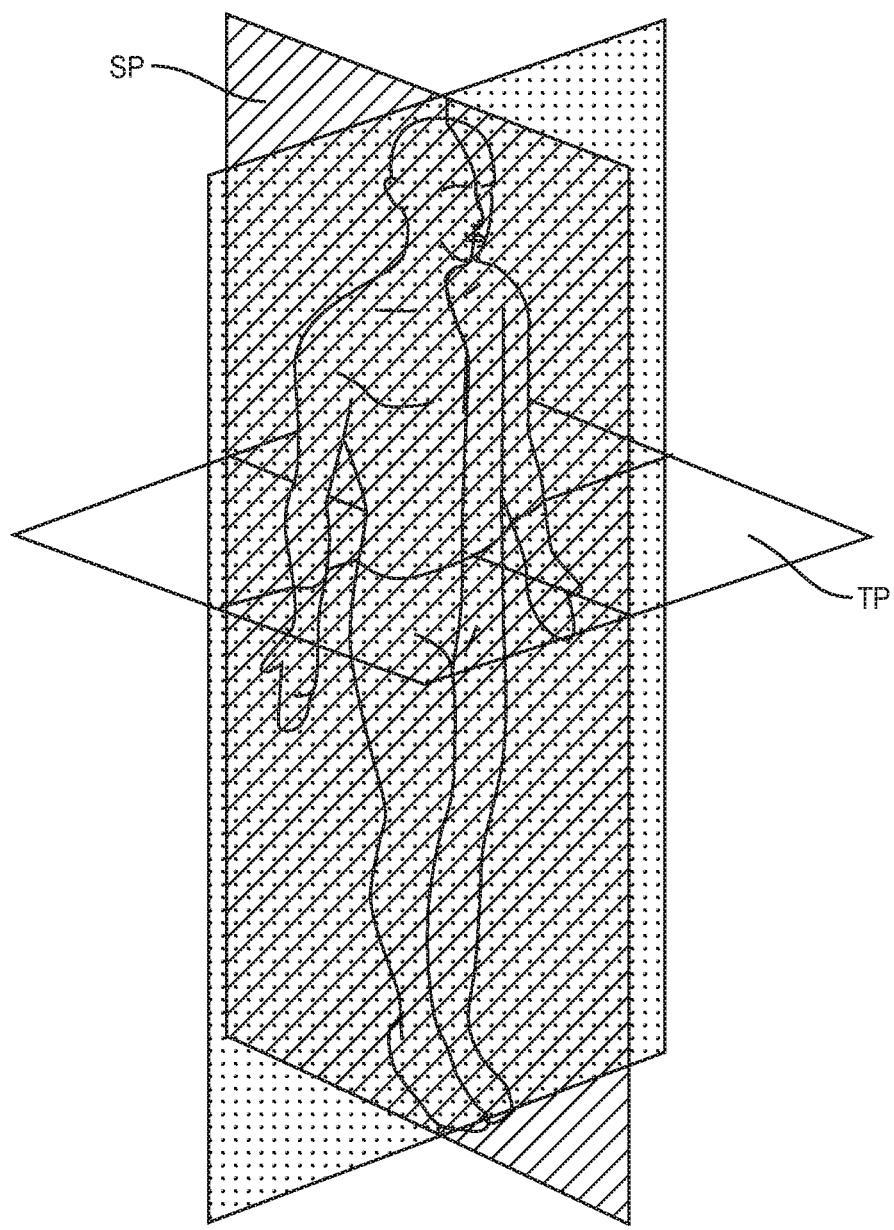
FIG. 16 is a perspective view of a patient anatomy.

Surface 44 of saddle 42 includes a wall 52 that defines a portion of cavity 24, as shown in FIGS. 3 and 9. Surface 44 defines a slot 54 configured for engagement with crown 32, for example, flange 40, as shown in FIG. 10. Slot 54 includes a track 56 defining an arcuate path of saddle 42 such that flange 40 can translate, for example, rotate within track 56. Track 56 defines a limit of rotation of saddle 42 relative to crown 32. Saddle 42 is movable relative to crown 32 in a plane, for example, a sagittal plane SP of a body, as shown in FIG. 16, such that flange 40 is relatively translatable in track 56 of slot 54, as shown in FIG. 10. In some embodiments, saddle 42 is configured for sagittal adjustment and/or movement forgiveness of spinal rod 26, as shown in FIG. 14. In some embodiments, all or only a portion of slot 54 may have alternate cross section configurations, for example, oval, oblong, triangular, square, polygonal, irregular, uniform, non-uniform, offset, staggered, and/or tapered. In some embodiments, crown 32 and surface 44/wall 52 of saddle 42 engage via an interference fit. In some embodiments, the interference fit includes a press assembly having a releasable friction fit.

Saddle 42 includes a top surface 58, as shown in FIGS. 3 and 10, which defines a curved portion configured for engagement with a spinal implant, for example, spinal rod 26. Surface 58 is configured to provide an axial grip with a spinal implant, for example, spinal rod 26. Saddle 42 is configured to provide flexion and/or extension strength to facilitate movement of spinal rod 26. In some embodiments, all or only a portion of surface 58 may have alternate cross section configurations, for example, oval, oblong, triangular, square, polygonal, irregular, uniform, non-uniform, offset, staggered, and/or tapered.

Figure 5:
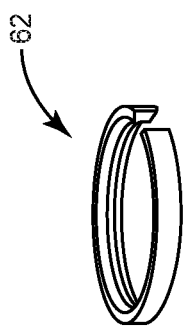
FIG. 5 is a perspective view of components of the system shown in FIG. 1.
Figure 6:
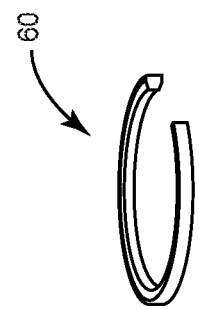
FIG. 6 is a perspective view of components of the system shown in FIG. 1.

Spinal implant system 10 includes a band, for example, a retaining ring 62 configured for provisional capture of head 50 of shaft 16, as shown in FIGS. 5 and 10 and/or fixed connection of the components of bone fastener 12, as described herein. Spinal implant system 10 includes a band, for example, a ring 60 configured for disposal in a contracted orientation and an expanded interference orientation adjacent to ring 62 to facilitate fixed connection of the components of bone fastener 12.

Receiver 14 includes portion 64, as shown in FIG. 10. Portion 64 includes a surface 66. Surface 66 defines a cavity, for example, a groove 68. Groove 68 is configured for disposal of ring 60. In some embodiments, groove 68 extends about all or a portion of surface 66. A surface 67 defines an expansion groove 69. Ring 60 includes a circumference that defines an opening, for example, a gap. In some embodiments, the gap is sized such that the gap has a thickness that is less than the height and the width. In some embodiments, the gap is sized to allow ring 60 to translate through a bottom of receiver 14 by contracting circumferentially. In some embodiments, all or only a portion of surface 66 may have alternate surface configurations, for example, rough, arcuate, undulating, mesh, porous, semi-porous, dimpled and/or textured.

Portion 64 includes a surface 70, as shown in FIG. 10. Surface 70 defines a cavity, for example, a groove 72. Groove 72 is configured for disposal of ring 62. Ring 62 includes a circumference that extends between ends of ring 62. In some embodiments, the ends define an opening, for example, a gap. In some embodiments, the gap is sized such that the gap has a thickness that is less than the height and the width. In some embodiments, the gap is sized to allow ring 62 to engage surface 70 by contracting circumferentially. In some embodiments, all or only a portion of surface 70 may have alternate surface configurations, for example, rough, arcuate, undulating, mesh, porous, semi-porous, dimpled and/or textured.

Receiver 14 and shaft 16 are engageable in a snap-fit assembly. In some embodiments, receiver 14 and shaft 16 are engageable in a pop-on assembly. In some embodiments, receiver 14 and shaft 16 are engageable in various fixation configurations, for example, friction fit, pressure fit, locking keyway and/or adhesive. As described above, shaft 16 includes flats 74 that are engageable with flats 49 of crown 32, as shown in FIGS. 1 and 11. Flats 74 are configured to interface in a keyed connection with flats 49 such that shaft 16 pivots through only the transverse plane relative to receiver 14. In some embodiments, head 50 includes one or more ridges, planar surfaces and/or arcuate surfaces to improve purchase of head 50 with crown 32.

Head 50 includes a tool engaging portion 76 configured to engage a surgical tool or instrument, as shown in FIG. 1 and described herein. In some embodiments, portion 76 includes a hexagonal cross-section. In some embodiments, portion 76 may have alternative cross-sections, for example, rectangular, polygonal, hexalobe, oval, or irregular.

Shaft 16 includes an outer surface 78 having an external thread form 80, as shown in FIG. 1. In some embodiments, the external thread form may include a single thread turn or a plurality of discrete threads. In some embodiments, other engaging structures may be located along surface 78, in place of or in addition to thread form 80 configurations discussed above, for example, a nail configuration, barbs, expanding elements, raised elements and/or spikes to facilitate engagement with tissue, for example, vertebral tissue. Alternatively, in some embodiments, surface 78 may have various surface configurations, for example, rough, arcuate, undulating, porous, semi-porous, dimpled, polished and/or textured.

In some embodiments, receiver 14 is selected from a plurality of alternate receivers 14 and bone screw shaft 16 via the mating surface is engageable with receiver 14 such that shaft 16 is interchangeable with a plurality of shafts 16.

In some embodiments, receiver 14 is manually engageable with shaft 16 in a non-instrumented assembly, as described herein. In some embodiments, manual engagement and/or non-instrumented assembly of receiver 14 and shaft 16 includes coupling without use of separate and/or independent instrumentation engaged with shaft 16 components to effect assembly. In some embodiments, manual engagement and/or non-instrumented assembly includes a practitioner, surgeon and/or medical staff grasping receiver 14 and shaft 16 and forcibly assembling the components. In some embodiments, manual engagement and/or non-instrumented assembly includes a practitioner, surgeon and/or medical staff grasping receiver 14 and shaft 16 and forcibly snap fitting the components together, as described herein. In some embodiments, manual engagement and/or non-instrumented assembly includes a practitioner, surgeon and/or medical staff grasping receiver 14 and shaft 16 and forcibly pop fitting the components together and/or pop fitting receiver 14 onto shaft 16, as described herein. In some embodiments, a force in a range of 2-50 N is required to manually engage receiver 14 and shaft 16 and forcibly assemble the components. For example, a force in a range of 2-50 N is required to snap fit and/or pop fit assemble receiver 14 and shaft 16. In some embodiments, a force in a range of 5-10 N is required to manually engage receiver 14 and shaft 16 and forcibly assemble the components. For example, a force in a range of 5-10 N is required to snap fit and/or pop fit assemble receiver 14 and shaft 16. In some embodiments, this configuration provides manually engageable components that are assembled without instrumentation, and subsequent to assembly, the assembled components have a selected pull-out strength and/or can be pulled apart, removed and/or separated with a minimum required force. In some embodiments, receiver 14 may be disposed with head 50 in alternate fixation configurations, for example, friction fit, pressure fit, locking protrusion/recess, locking keyway and/or adhesive.

In some embodiments, spinal implant system 10 comprises a spinal implant kit, as described herein, which includes a plurality of shafts 16 and/or receivers 14. Shaft 16 and/or receiver 14 is configured for selection such that the components of bone fastener 12 are interchangeable in a configuration having a range of motion that is restricted to a single plane, for example, the transverse plane.

In assembly, operation and use, spinal implant system 10, similar to the systems and methods described herein, includes shaft 16 for connection with receiver 14, and is employed with a surgical procedure for treatment of a spinal disorder affecting a section of a spine of a patient, as discussed herein. Spinal implant system 10 is employed with a surgical procedure for treatment of a condition or injury of an affected section of the spine.

In some embodiments, shaft 16 is selected from a kit of a plurality of shafts 16 for interchangeable connection with receiver 14 to include a bone fastener where receiver 14 is rotatable relative to shaft 16 in a transverse plane TP of a body and saddle 42 is movable relative to crown 32 in a sagittal plane SP of the body such that crown 32 is translatable in slot 54. In some embodiments, the kit of shaft 16 includes a variety of shafts 16 having different movement configurations when assembled with an interchangeable receiver 14, for example, multi-axial movement, sagittal angulation movement, fixed axis movement, mono-axial movement and/or uni-planar movement.

Figure 15:
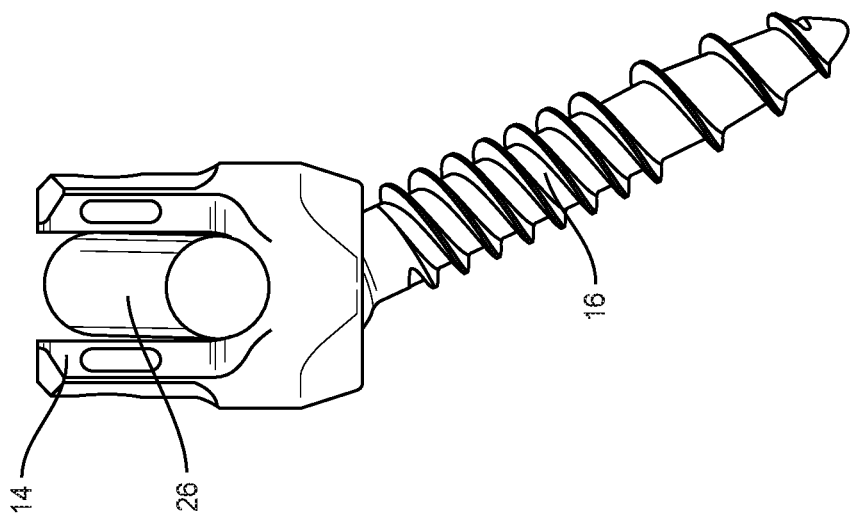
FIG. 15 is a side view of the components shown in FIG. 14.

In some embodiments, receiver 14 is assembled with crown 32, saddle 42, ring 60 and ring 62, as shown in FIGS. 1, and 7-10. Ring 62 is disposed with groove 72 and ring 60 is disposed with groove 68 in a contracted orientation, as shown in FIG. 10. Shaft 16 is engageable, as described herein, with receiver 14, as shown in FIG. 15. Receiver 14 is assembled with shaft 16 by translating receiver 14, in a direction shown by arrow A in FIG. 1. Engagement of head 50 with receiver 14 causes a surface of head 50 to engage with ring 62 such that ring 62 is translated, in a direction shown by arrow C in FIG. 1, disposing ring 62 into groove 69 in an expanded orientation. Head 50 translates further through receiver 14 in a direction shown by arrow B in FIG. 10 and passes further through ring 62 as ring 62 is driven back into groove 72. Ring 62 resiliently contracts into its natural state around head 50 as flats 74 engage with recess 48 to provisionally capture shaft 16, as shown in FIGS. 1, 10 and 11.

Figure 8:
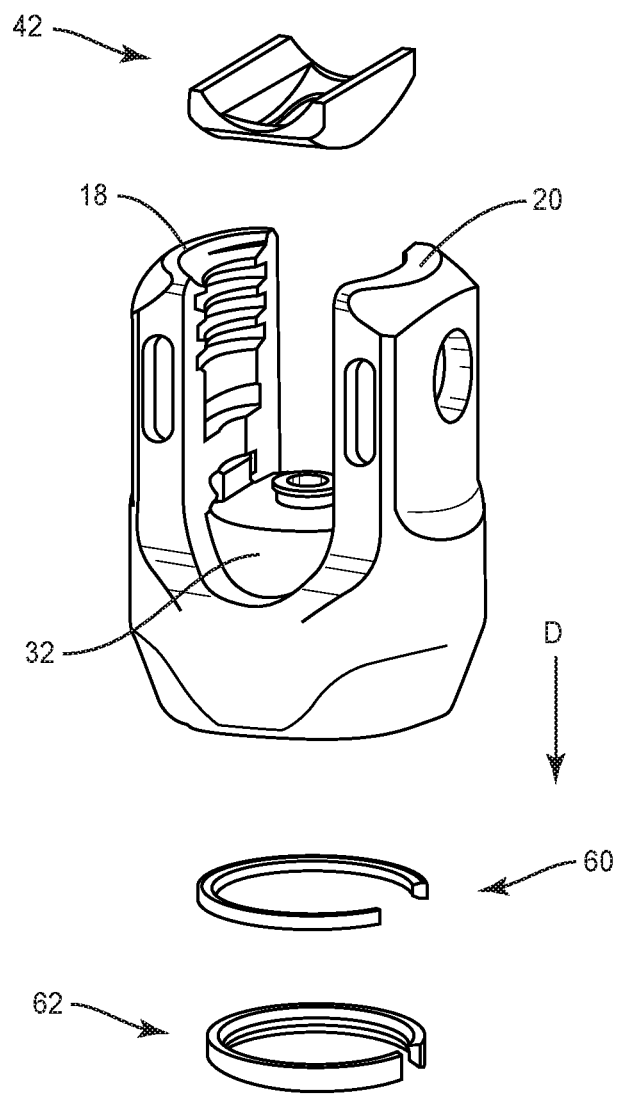
FIG. 8 is a perspective view of components of one embodiment of a spinal implant system in accordance with the principles of the present disclosure with parts separated.

Crown 32 is manipulated, for example, via engagement by a surgical instrument to translate crown 32, in a direction shown by arrow D in FIG. 8. Surface 38 of crown 32 engages ring 60 to dispose ring 60 into groove 69 such that ring 60 resiliently opens into an expanded orientation. Ring 60 is oriented for abutting and/or contacting engagement with ring 62 to resist and/or prevent translation of ring 62 from groove 72 into groove 69, and thus providing fixed connection of the components of bone fastener 12 including permanent capture of head 50 and shaft 16 in a configuration having a range of motion that is restricted to a single plane, for example, in a uni-axial movement configuration.

Saddle 42 is manipulated, for example, via engagement by a surgical instrument to translate saddle 42, in a direction shown by arrow E in FIG. 9. Saddle 42 engages crown 32 via slot 54 and flange 40 in an interference fit, for example, a snap fit engagement, as shown in FIG. 10. When engaged, saddle 42 is movable relative to crown 32 in a sagittal plane SP of a body, as shown in FIG. 16 such that crown 26 is translatable in slot 54. In some embodiments, during manufacturing, saddle 42 is positioned with crown 32 via a manufacturing press and/or press fit. In some embodiments, crown 32 is configured to provide an increase in axial grip on spinal rod 26 and an increase in flexion and/or extension strength.

In use, for treatment of a spinal disorder, bone fastener 12 including shaft 16 and receiver 16 can be threaded and engaged with tissue. In some embodiments, bone fastener 12 is disposed adjacent vertebrae V at a surgical site and is manipulated to drive, torque, insert or otherwise connect shaft 16 with vertebrae V1 and V2 in connection with a surgical procedure, as described herein. Receiver 14 is rotatable relative to shaft 16 in a transverse plane TP of a body and saddle 42 is movable relative to crown 32 in a sagittal plane SP of the body such that crown 32 is translatable in slot 54, as shown in FIGS. 14-17.

In one embodiment, as shown in FIGS. 12-13, spinal implant system 10 includes a bone fastener 112, similar to bone fastener 12 described herein, which includes a receiver 114, similar to receiver 14 and a shaft 116, similar to shaft 16. Receiver 114 is rotatable relative to shaft 116 in a plane, for example, a transverse plane TP of a body. Receiver 114 extends along and defines an axis X2, as shown in FIG. 12.

Receiver 114 includes a part, for example, a crown 132, similar to crown 32, a saddle 142, similar to saddle 42, a retaining ring 160, similar to retaining ring 60 and retaining ring 162, similar to retaining ring 62, as shown in FIG. 13. Crown 132 is configured for disposal within a cavity 124, similar to cavity 24, as shown in FIGS. 12-13. Crown 132 is non-rotatable or fixed in rotation relative to a surface 122 that defines cavity 124. Crown 32 includes a circumferential wall 134 having an end surface 136 and an end surface 138.

Surface 136 defines a recess 141, as shown in FIG. 13. Recess 141 is configured for engagement with a surface 144 of saddle 142 and a projection, for example, a retention member 145 as shown in FIG. 12 and described herein. In some embodiments, all or only a portion of recess 141 may have alternate cross section configurations, for example, oval, oblong, triangular, square, polygonal, irregular, uniform, non-uniform, offset, staggered, and/or tapered.

Surface 144 of saddle 142 defines a wall 152 that defines a portion of cavity 124, as shown in FIGS. 12-13. Surface 144 defines a slot 154 configured for engagement with retention member 145, as shown in FIGS. 12-13. Retention member 145 is configured to retain saddle 142 with crown 132 and to limit angular rotation of saddle 142 when disposed in receiver 114. In some embodiments, a surface 147 of retention member 145 is welded to crown 132. In some embodiments, retention member 145 includes a press fit or a threaded connection with crown 132 and/or saddle 142. Saddle 142 is movable relative to crown 132 in a plane, for example, a sagittal plane SP of a body, as shown in FIG. 16. In some embodiments, all or only a portion of retention member 145 may have alternate cross section configurations, for example, oval, oblong, triangular, square, polygonal, irregular, uniform, non-uniform, offset, staggered, and/or tapered.

In some embodiments, spinal implant system 10 includes an agent, which may be disposed, packed, coated or layered within, on or about the components and/or surfaces of spinal implant system 10. In some embodiments, the agent may include bone growth promoting material, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

In some embodiments, the use of microsurgical and image guided technologies may be employed to access, view and repair spinal deterioration or damage, with the aid of spinal implant system 10. The components of spinal implant system 10 can be made of radiolucent materials such as polymers. Radiomarkers may be included for identification under x-ray, fluoroscopy, CT or other imaging techniques.

In some embodiments, spinal implant system 10 can include one or a plurality of bone fasteners 12 such as those described herein and/or fixation elements, which may be employed with a single vertebral level or a plurality of vertebral levels. In some embodiments, bone fasteners 12 may be engaged with vertebrae in various orientations, for example, series, parallel, offset, staggered and/or alternate vertebral levels. In some embodiments, bone fasteners 12 may be configured as multi-axial screws, sagittal angulation screws, pedicle screws, mono-axial screws, uni-planar screws, fixed screws, anchors, tissue penetrating screws, conventional screws, expanding screws. In some embodiments, bone fasteners 12 may be employed with wedges, anchors, buttons, clips, snaps, friction fittings, compressive fittings, expanding rivets, staples, nails, adhesives, posts, connectors, fixation plates and/or post.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone fastener comprising:
   a first member comprising a first surface defining an implant cavity, the first member including a first part being non-rotatable relative to the first surface and a second part including a second surface defining a portion of the implant cavity and a slot, the first part comprising a projection and a circumferential flange extending 360 degrees about the projection; and
   a second member being configured to penetrate tissue and connectable with the first member,
   wherein the first member is rotatable relative to the second member in a first plane of a body and the second part is movable relative to the first part in a second plane of the body such that the first part is relatively translatable in the slot, and wherein the first part is engaged in an interference fit with the second part.

2. A bone fastener as recited in claim 1, wherein the interference fit includes a press assembly having a releasable friction fit.

3. A bone fastener as recited in claim 1, wherein the projection and the flange are engaged in the interference fit with the second part.

4. A bone fastener as recited in claim 1, wherein the first part includes a body including a proximal wall and a side wall extending 360 degrees about the proximal wall, the projection being welded to the proximal wall.

5. A bone fastener as recited in claim 4, wherein the first part comprises spaced apart arms each extending proximally from the proximal wall.

6. A bone fastener as recited in claim 5, wherein a distal portion of the second part is positioned entirely between the arms.

7. A bone fastener as recited in claim 1, wherein the first member comprises a first groove, a second groove and a third groove, the third groove being positioned between the first groove and the second groove, the bone fastener comprising a first band positioned in the first groove and a second band positioned in the second groove, the first band being configured to movable from the first groove to the third groove such that the members are engageable in a snap-fit assembly.

8. A bone fastener as recited in claim 1, wherein the first member comprises a first groove, a second groove and a third groove, the third groove being positioned between the first groove and the second groove, the bone fastener comprising a first band positioned in the first groove and a second band positioned in the second groove, the first band being configured to movable from the first groove to the third groove such that the members are engageable in a pop-on assembly.

9. A bone fastener as recited in claim 1, wherein the slot includes a track defining an arcuate path of the second part.

10. A bone fastener as recited in claim 1, wherein the second member includes flats engageable with the first part that interface in a keyed connection such that the second member pivots through only the first plane relative to the first member.

11. A bone fastener as recited in claim 1, wherein the second part includes opposite proximal and distal surfaces, the slot extending through the proximal and distal surfaces, the flange including opposite proximal and distal surfaces, the projection extending through the slot such that the distal surface of the flange directly engages the proximal surface of the second part.

12. A bone fastener comprising:
a receiver comprising an inner surface defining an implant cavity, the receiver including a crown fixed in rotation with the inner surface and a saddle including a wall defining a portion of the implant cavity and a slot, the crown comprising a projection and a circumferential flange extending outwardly from the projection, the flange extending 360 degrees about the projection; and
a bone screw shaft including a head having a mating element engageable with the crown,
wherein the receiver is rotatable relative to the shaft in a transverse plane of a body and the saddle is movable relative to the crown in a sagittal plane of the body such that the crown is translatable in the slot, and
wherein the crown is engaged in an interference fit with the wall, the interference fit including a press assembly having a releasable friction fit.

13. A bone fastener as recited in claim 12, wherein the projection and the flange are engaged in the interference fit with the wall.

14. A bone fastener as recited in claim 12, wherein the crown includes a body including a proximal wall and a side wall extending 360 degrees about the proximal wall, the projection being welded to the proximal wall.

15. A bone fastener as recited in claim 12, wherein the receiver and the shaft are engageable in a snap-fit assembly.

16. A bone fastener as recited in claim 12, wherein the slot includes a track defining an arcuate path of the saddle.

17. A bone fastener as recited in claim 12, wherein the mating element includes flats engageable with the crown that interface in a keyed connection such that the shaft pivots through only the transverse plane relative to the receiver.

18. A bone fastener comprising:
a first member comprising a first surface defining an implant cavity, the first member including a first part being non-rotatable relative to the first surface and a second part including a second surface defining a portion of the implant cavity and a slot, the first part comprising a projection and a circumferential flange extending 360 degrees about the projection; and
a second member being configured to penetrate tissue and connectable with the first member,
wherein the first member is rotatable relative to the second member in a first plane of a body and the second part is movable relative to the first part in a second plane of the body such that the first part is relatively translatable in the slot, and
wherein the first part includes a body including a proximal wall and a side wall extending 360 degrees about the proximal wall, the projection being welded to the proximal wall, the first part further comprising spaced apart arms each extending proximally from the proximal wall.

* * * * *